US005763190A

United States Patent [19]

Weiner et al.

[11] Patent Number: 5,763,190
[45] Date of Patent: Jun. 9, 1998

[54] METHODS FOR THE IDENTIFICATION OF COMPOUNDS CAPABLE OF INDUCING THE NUCLEAR TRANSLOCATION OF A RECEPTOR COMPLEX COMPRISING THE GLUCOCOTICOID RECEPTOR TYPE II AND VIRAL PROTEIN R INTERACTING PROTEIN

[75] Inventors: David B. Weiner, Merion, Pa.; Yosef Refaeli, Boston, Mass.

[73] Assignee: The Trustees of the University of Pennsylvania, Philadelphia, Pa.

[21] Appl. No.: 309,644

[22] Filed: Sep. 21, 1994

[51] Int. Cl.$^6$ .......................... G01N 33/53; C12P 21/06; C12N 15/00
[52] U.S. Cl. .......................... 435/7.1; 435/7.8; 435/69.1; 435/172.3
[58] Field of Search .......................... 475/7.1, 7.8, 69.1, 475/172.3; 436/501

[56] References Cited

U.S. PATENT DOCUMENTS

| | | | |
|---|---|---|---|
| 5,346,696 | 9/1994 | Kim et al. | 424/85.4 |
| 5,391,723 | 2/1995 | Priest | 536/23.1 |

OTHER PUBLICATIONS

Agarwal, et al., 1987, Glucocorticoid Antagonists. FEBS letters. 217, 221–226.
Bakke, 1986, Antagonistic effect of glucocorticoids on retinoic acid induced growth inhibition and morphological alterations of a human cell line. Cancer Res. 46, 1275–1279.
Balotta, et al., 1993, Antisense phosphorothioate oligodeoxynucleotides targeted to the vpr gene inhibit human immunodeficiency virus type 1 replication in primary human macrophages. J. Virol. 67, 4409–4414.
Baulieu, 1991, The Steroid Hormone Antagonist RU486. Endocrinology and Metabolism. 20, 873.
Beato, 1989, Gene regulation by steroid hormones. Cell. 56, 335–344.
Bodine and Litwack, 1990 The glucocorticoid receptor and its endogenous regulators. Receptor. 1, 83–120.
Cohen, et al., 1990, Human immunodeficiency virus vpr, product is a virion–associated regulatory protein. J. Virol. 64, 3097–3099.
Cohen, et al., 1990, Identification of HIV–1 vpr product and function. J. AIDS. 3, 11–18.
Dedera, et al., 1989, Viral protein R of human immunodeficiency virus types 1 and 2 is dispensable for replication and cytopathogenicity in lymphoid cells. J. Virol. 63, 3205–3208.
Dietrich, et al., 1986, Antagonism of glucocorticoid induction of Epstein–Barr virus early antigens by different steroids in Daudi lymphoma cells. J. Steroid Biochem. 24, 417–421.
Evans, 1988, The Steroid and Thyroid Hormone Receptor Superfamily. Science. 240, 889–895.
Ghosh, 1992, Glucocorticoid Receptor Binding Site in the Human Immunodeficiency Virus Long Terminal Repeat. J. Virol. 66, 586–590.

Gorman, et al., 1982, The Rous sarcoma virus long terminal repeat is a strong promoter when introduced into a variety of eukaryotic cells by DNA mediated transfection. Proc. Natl. Acad. Sci. USA. 79, 6777–6781.
Green and Chambon, 1988, Nuclear receptors enhance our understanding of transcription regulation. Trends. Genet. 4, 309–314.
Gronemeyer, et al., 1992, Mechanisms of Antihormone Action. J. Steroid Biochem. 41, 217–221.
Haseltine, 1991, Molecular biology of the human immunodeficiency virus type 1. FASEB J. 5, 2349–2360.
Hattori, et al., 1990, The human immunodeficiency virus type 2 vpr gene is essential for productive infection of human macrophages. Proc. Natl. Acad. Sci. USA. 87, 8080–8084).
Katsanakis, et al., 1991, The human immunodeficiency virus long terminal repeat contains sequences showing partial homology to glucocorticoid response elements. Anticancer Res. 11, 381–383.
Koenig, et al., 1986, Detection of AIDS virus in macrophages in brain tissue from AIDS patients with encephalopathy. Science. 233, 1089–1093.
Kolesnitchenko and Snart, 1992, Regulatory Elements in the Human Immunodeficiency Virus Type 1 Long Terminal Repeat LTR(HIV–1) Responsive to Steroid Hormone Stimulation. AIDS Res. Hum. Retrov. 8, 1977.
Lang, et al., 1993, Importance of vpr for infection of rhesus monkeys with simian immunodeficiency virus. J. Virol. 67, 902–912.
Laurence, et al., 1990, Effect of glucocorticoids on chronic human immunodeficiency virus (HIV) infection and HIV promoter–mediated transcription. Blood. 74, 291–297.
Miksicek, et al., 1986, Glucocorticoid responsiveness of the transcriptional enhancer of Moloney murine sarcoma virus. Cell. 46, 283–290.

(List continued on next page.)

*Primary Examiner*—Donald E. Adams
*Assistant Examiner*—Jeffrey S. Parkin
*Attorney, Agent, or Firm*—Woodcock Washburn Kurtz Mackiewicz & Norris LLP

[57] ABSTRACT

Human immunodeficiency virus (HIV)-1, HIV-2, and simian immunodeficiency virus contain, in addition to the canonical gag/pol/env genes, additional small open reading frames encoding gene products, including the 96-amino acid 15-kDa virion associated HIV-1 Vpr gene product. The conservation of the vpr open reading frame in primate lentiviruses suggests that vpr is critical to viral replication. A biologically active recombinant HIV-1 Vpr protein was employed as a ligand to identify its cellular targets. A novel 41-kDa cytosolic protein was identified and termed the viral protein R interacting protein, or Rip-1. Rip-1 displays a wide tissue distribution, including relevant targets of HIV infection. Vpr protein induced nuclear translocation of Rip-1, as did glucocorticoid receptor (GR)-II-stimulating steroids. Vpr and Rip-1 coimmunoprecipitated with the human GR as part of a receptor complex. The present invention discloses methods for the identification of compounds capable of inducing GR-II/Rip-1 receptor complex cytosolic to nuclear translocation.

5 Claims, No Drawings

OTHER PUBLICATIONS

Lavallee, et al., 1994, Requirement of the Pr55gag precursor for incorporation of the Vpr product into Human Immunodeficiency Virus type 1 Viral Particles. J. Virol. 68, 1926–1934.

Lazar and Agarwal, 1986, Evidence for an antagonist specific receptor that does not bid mineralocorticoid agonists. Biochem Biophys Res Commun. 134, 261–265.

Levy, et al., 1993, Induction of cell differentiation by human immunodeficiency virus 1 vpr. Cell. 72, 541–550.

Levy, David N. et al., 1994, Serum vpr regulates HIV–1 latency Proc. Nat. Acad. Sci. USA. 91: 10873–10877.

Lindenmeyer, et al., 1990, Glucocorticoid Receptor Monoclonal Antibodies Define the Biological Action of RU38486 in Intact 1316 Melanoma Cells. Cancer Res. 50, 7985–7991.

Lu, et al., 1993, Human immunodeficiency virus type 1 viral protein R localization in infected cells and virions. J. Virol. 67, 6542–6550.

Madan and DeFranco, 1993, Bidirectional transport of glucocorticoid receptors across the nuclear envelope. Proc. Natl. Acad. Sci. USA. 90, 3588–3592.

Merrifield, "Solid Phase Peptide Synthesis. I. The Synthesis of a Tetrapeptide" *J. Am. Chem. Soc.*, 15:2149–2154 (1963).

Newmeyer and Forbes, 1988 Nuclear import can be separated into distinct steps in vitro: nuclear pore binding and translocation. Cell. 52, 641–653.

Ogawa, et al., 1989, Mutational analysis of the human immunodeficiency virus vpr open reading frame. J. Virol. 63, 4110–4114.

Parker, 1992, Introduction; Growth Regulation by Nuclear Hormone Receptors. Cancer Surv. 14, 1–4.

Paxton, et al., 1993, Incorporation of vpr into human immunodeficiency virus type 1 virions: requirement for the p6 region of gag and mutational analysis. J. Virol. 67, 7229–7237.

Perrot–Applanat, et al., 1992, Immunolocalization of steroid hormone receptors in Normal and Tumour Cells: Mechanisms of their cellular traffic. Cancer Surv. 14, 5–30.

Picard and Yamamoto, 1987, Two signals mediate hormone–dependent nuclear localization, of the glucocorticoid receptor. EMBO. 6(11), 3333–3340.

Richardson, et al., 1988, Nuclear protein migration involves two steps: rapid binding at the nuclear envelope followed by slower translocation through nuclear pores. Cell. 52, 655–664.

Shibata, et al., 1990, Mutational analysis of the human immunodeficiency virus type 2 (HIV–2) genome in relation to HIV–1 and simian immunodeficiency virus $SIV_{AGM}$. J. Virol. 64, 742–747.

Weiner, 1989, A point mutation in the neu oncogene mimics ligand induction. Nature. 339, 230–231.

Westervelt, et al., 1992, Dual regulation of silent and productive infection in monocytes by distinct human immunodeficiency virus type 1 determinants. J. Virol. 66, 3925–3931.

Yuan, et al., 1990, Human immunodeficiency virus vpr gene encodes a virion–associated protein. AIDS Res. Hum. Retrovir. 6, 1265–1271).

Zwerner, et al. 1979 Cell Culture, Eds. Jakoby and Pastan, Ch. 18, pp. 221–229 (*Methods in Enzymology vol. 58*) Academic Press, San Diego, CA.

Zhao et al., "Biochemical Mechanism of HIV–1 Vpr Function" J. Biol. Chem. 269: 15577–15582 (1994).

Rogel, M. et al., "The Human Immunodeficiency Virus Type 1 vpr Gene Prevents Cell Proliferation during Chronic Infection", *J. of Virology* 1995, 69(2), 882–888.

Phizicky et al., 1995, Microbiol. Rev. 59:94–123.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

TGTTCT        6

( 2 ) INFORMATION FOR SEQ ID NO:2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GATCCGGCCC AATAAAGGAG AGAACACCAG CTTGTTACAC CCTGTGAG    48

( 2 ) INFORMATION FOR SEQ ID NO:3:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GATCCTCACA GGGTGTAACA AGCTGGTGTT CTGTCCTTTA TTGGCCG    47

-continued ( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GATCCGTTTA TGGTTACAAA CTGTTCTTAA AACAAG        36

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GATCCTTGTT TTAAGAACAG TTTGTAACCA TAAACG        36

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GATCCATTAG TTGCTAGGCA ACTGGCG        27

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GATCCGCCAG TTGCCTAGCA ACTAATG        27

METHODS FOR THE IDENTIFICATION OF COMPOUNDS CAPABLE OF INDUCING THE NUCLEAR TRANSLOCATION OF A RECEPTOR COMPLEX COMPRISING THE GLUCOCOTICOID RECEPTOR TYPE II AND VIRAL PROTEIN R INTERACTING PROTEIN

CROSS REFERENCE TO RELATED PATENT APPLICATIONS

This application is related to U.S. patent application Ser. No. 08/167,519 filed Dec. 15, 1993, pending, and U.S. patent application Ser. No. 08/246,177 filed May 19, 1994, pending, the disclosures of each of which are incorporated herein by reference in their entirety. In addition, U.S. Ser. No. 08/019,601 filed Feb. 19, 1993, U.S. Ser. No. 08/167,608 filed Dec. 15, 1993, and PCT Patent Application Number PCT/US94/02191 filed Feb. 22, 1994 are each incorporated herein by reference.

FIELD OF THE INVENTION

The present invention relates to compounds which modulate glucocorticoid receptor-complex transactivation activity. The present invention relates to a method of identifying compounds which stimulate GR complex transactivation. The present invention relates to a method of identifying compounds which inhibit GR-complex transactivation. The present invention relates to methods of evaluating the level of infection of individuals infected with human immunodeficiency virus (HIV). The present invention relates to transfection agent, particularly for the delivery of nucleic acid molecules or derivatives thereof into the nucleus of a cell.

BACKGROUND OF THE INVENTION

Primate lentiviruses, HIV-1, HIV-2 and SIV, contain, in addition to the canonical gag/pol/env genes, six additional small open reading frames encoding gene products which assist in the viral life cycle. Among these the function of the 96 amino acid Vpr protein remains poorly defined.

The vpr gene of HIV-1 encodes a 15 kD virion-associated polypeptide. Probably all the primate lentiviruses contain a vpr gene whose amino acid sequence is highly conserved within these groups. The conservation of the vpr open reading frame in evolution suggests that Vpr carries a function which is nondispensable for the viral lifecycle in vivo, though potentially dispensable for replication in certain cell lines in vitro. The incorporation of Vpr into virions (Cohen, et al., 1990a, Human immunodeficiency virus Vpr, product is a virion-associated regulatory protein. J. Virol. 64, 3097–3099; Yuan, et al., 1990, Human immunodeficiency virus vpr gene encodes a virion-associated protein. AIDS Res. Hum. Retrovir. 6, 1265–1271) as well as its cellular co-localization with Gag (Lu, et al., 1993, Human immunodeficiency virus type 1 viral protein R localization in infected cells and virions. J. Virol. 67, 6542–6550; Paxton, et al., 1993, Incorporation of Vpr into human immunodeficiency virus type 1 virions: requirement for the p6 region of Gag and mutational analysis. J. Virol. 67, 7229–7237; Lavallee, et al., 1994, Requirement of the Pr55gag precursor for incorporation of the Vpr product into Human Immunodeficiency Virus type 1 Viral Particles. J. Virol. 68, 1926–1934), has led to speculation that Vpr performs a structural role in the virus particle. However, vpr deletion mutant viruses produce virions which appear normal in electron micrographs (Terwilliger, 1992, The accessory gene functions of the primate immunity viruses. in: AIDS Research Reviews, Vol. 2. Koff, W. C., Wong-Staal, F. and Kennedy, R. C. (New York, N.Y.: Marcel Dekker, Inc.) and vpr deletion mutant viruses remain infectious with somewhat lower replication kinetics in the majority of CD4+ T cell lines analyzed in vitro (Dedera, et al., 1989, Viral protein R of human immunodeficiency virus types 1 and 2 is dispensable for replication and cytopathogenicity in lymphoid cells. J. Virol. 63, 3205–3208; Shibata, et al., 1990, Mutational analysis of the human immunodeficiency virus type 2 (HIV-2) genome in relation to HIV-1 and simian immunodeficiency virus $SIV_{AGM}$. J. Virol. 64, 742–747; Ogawa, et al., 1989, Mutational analysis of the human immunodeficiency virus vpr open reading frame. J. Virol. 63, 4110–4114; Cohen, et al., 1990b, Identification of HIV-1 Vpr product and function. J. AIDS. 3, 11–18). The presence of Vpr in the viral particle is consistent with its possible role early in infection. It has been suggested that delivery of Vpr into cells by virus could increase cellular permissiveness to early events in virus replication.

The vpr gene of HIV-1 is sufficient to induce growth arrest and cellular differentiation in rhabdomyosarcoma and osteosarcoma cells which express it, either following infection with HIV-1 virus or by transfection of the vpr gene alone, indicating that Vpr is a regulator of cellular events linked to virus production (Levy, et al., 1993, Induction of cell differentiation by human immunodeficiency virus 1 Vpr. Cell. 72, 541–550). It has been reported that viral replication in macrophages can be inhibited by vpr antisense ribonucleotides (Balotta, et al., 1993, Antisense phosphorothioate oligodeoxynucleotides targeted to the vpr gene inhibit human immunodeficiency virus type 1 replication in primary human macrophages. J. Virol. 67, 4409–4414). In contrast to the kinetics observed in T cell lines in vitro, vpr deletion mutants are poorly infectious in myeloid lines in vitro (Westervelt, et al., 1992, Dual regulation of silent and productive infection in monocytes by distinct human immunodeficiency virus type 1 determinants. J. Virol. 66, 3925–3931; Nattori, et al., 1990, The human immunodeficiency virus type 2 vpr gene is essential for productive infection of human macrophages. Proc. Natl. Acad. Sci. USA. 87, 8080–8084) indicating an important function for Vpr in infection of this lineage. In trans, the Vpr protein increases virus replication in T lymphocytes and monocyte/macrophages in vitro (Levy, et al., 1994b, Extracellular Vpr as a positive regulator of HIV-1 expression, (submitted)), although the effects on monocytes/macrophages was clearly greater. Importantly, nef-, vpr- mutant SIV replicated poorly in nonhuman primates (Lang, et al., 1993, Importance of Vpr for infection of rhesus monkeys with simian immunodeficiency virus. J. Virol. 67, 902–912). The presence of Vpr protein in serum of HIV+ individuals has been reported, and it has been demonstrated that purified serum-derived Vpr reactivates HIV-1 replication in latently infected cell lines and in primary hematopoietic cells (Levy, et al., 1994a, Serum Vpr regulates HIV-1 latency. Proc. Nat. Acad. Sci. USA. In press).

The molecular mechanism by which Vpr exerts its effects is not known. Transfection studies have shown that Vpr is a weak transactivator of the HIV LTR and several other heterologous viral promoters, including HTLV-1, EBV, and CMV (Cohen, et al., 1990b, supra). These observations, and the fact that Vpr is packaged into virions, have lead some to propose that Vpr may function as an activator of viral mRNA transcription in the pre-transcriptional tat independent stage (Haseltine, 1991, Molecular biology of the human immunodeficiency virus type 1. FASEB J. 5, 2349–2360).

Glucocorticoid receptors are members of a superfamily of receptor molecules which are involved in the development, differentiation and general maintenance of homeostasis in lieu of a host of stimuli. These ligand-dependant transcription factors have been shown to upregulate the expression of reporter genes superseded by the LTR sequences of HIV as well as those from other retroviruses. In addition, glucocorticosteroids have been studied for their ability to reactivate HIV gene expression in nonproductively infected, or latent cell lines. This reactivation from latency could be prevented by the exposure of those latent cells to agents such as DHEA, a steroid with many functions, among which is the competitive blocking of the action of glucocorticosteroids. In addition, glucocorticoid response element (GRE) sequences have been shown to exist within the HIV LTR, by footprinting as well as by DNAse protection and gel retardation assays. However no direct link between the glucocorticoid biochemical pathway and the HIV lifecycle had been established.

The ability of Vpr to regulate target cells as seen by the Vpr induced cellular differentiation as well as the cessation of proliferation (Levy, et al., 1993, supra), strongly suggests that Vpr mediates its biological activity through a direct interaction with a cellular biochemical pathway. Vpr protein expressed in insect cells using recombinant baculoviruses and observed that this protein mediated cellular differentiation, reactivated virus expression from virally infected cells (Levy, et al., 1994a, supra), increased cellular permissiveness to new infection (Levy, et. al., 1994b, supra), and complemented HIV-1 infection of myeloid cell lines (Levy, et. al. 1994a, supra; Levy et. al., 1994b, supra). Accordingly, this protein was used as a ligand to identify putative cellular targets of Vpr.

SUMMARY OF THE INVENTION

The present invention relates to methods of identifying compounds that induce GR type II complex translocation. The methods of the present invention comprise the steps of first contacting cells that comprise Rip-1 and GR type II complex with a test compound and then detecting whether or not Rip-1 translocates from the cytoplasm to the nucleus of the cell. According to some embodiments of the invention, Rip-1 translocation is detected by isolating the cytoplasm of the cell from the nucleus and detecting the presence of Rip-1 in the nucleus by contacting the nucleus with antibodies that bind to Rip-1 and the detecting said antibodies.

The present invention relates to methods of translocating GR type II complex in cells which comprise GR type II complex and Rip-1. The methods comprise the step of administering to the cells, a composition comprising Vpr protein or a Rip-1 binding fragment thereof which induces Rip-1 translocation.

The present invention relates to methods of identifying individuals infected with human immunodeficiency virus. The diagnostic and prognostic methods of the invention comprise the steps of contacting cells that comprise Rip-1 and GR type II complex with a test compound with a sample form an individual and detecting whether or not Rip-1 translocates from the cytoplasm to the nucleus of the cell or detecting whether or not glucocorticoid receptor protein translocates from the cytoplasm to the nucleus of the cell. In some embodiments, the cytoplasm of the cell is isolated from the nucleus and the presence of Rip-1 and/or glucocorticoid receptor protein in the nucleus is detected using antibodies. In some embodiments, the cells comprise a gene construct that comprises a marker gene operably linked to regulatory elements that include a glucocorticoid response element sequence and translocation of Rip-1 and glucocorticoid receptor protein from the cytoplasm to the nucleus of the cell is detected by detecting expression of the marker gene.

The present invention relates to conjugated compositions that comprise a first moiety which comprises isolated Vpr or a Rip-1-binding fragment thereof covalently linked to a second moiety which comprises an active agent selected from the group consisting of a drug, a toxin, a nucleic acid molecule and a radioisotope.

DETAILED DESCRIPTION OF THE INVENTION

The vpr gene has been shown to increase the kinetics of viral replication and cytopathicity in T lymphocytes (Cohen, et al., 1990b, supra), and may be necessary for the productive infection of macrophages (Nattori, et al., 1990, supra; Westervelt, et al., 1992, supra) and the regulation of HIV-1 cellular latency (Levy, et al., 1994a, supra; Levy, et al., 1994b, supra). The vpr gene of HIV-1 induces the cessation of cellular proliferation, as well as cellular differentiation in rhabdomyosarcoma and osteosarcoma cell lines (Levy, et al., 1993, supra). The precise mechanism of Vpr function however in not clear.

Vpr has been reported to accumulate in the cell nucleus in the process of infection (Lu, et al., 1993, supra). This is consistent with the weak LTR transactivating activity which has been reported for Vpr (Cohen, et al., 1990b, supra). Along these lines Vpr can profoundly change the state of the host cell presumably through modification of the host cell gene expression. Such changes require the interaction of Vpr with cellular biochemical pathways.

A 41 kD cytosolic protein (Rip-1) which interacts with HIV-1 viral protein R has been identified. Rip-1 and Vpr coeluted from a Vpr-specific immunoaffinity column as well as from a Vpr protein column. In addition, the complex formed by Vpr and Rip-1 was reversibly crosslinked to a 58 kD complex. Rip-1 was found to be constitutively expressed in a wide variety of cell lines derived from tissues which are targets of HIV infection.

Rip-1 was observed to co-translocate with Vpr into the nucleus either after the exposure of the cells to HIV-1 virus, or to exogenous Vpr protein. This nuclear translocation of Rip-1 however was not induced by a Vpr mutant virus nor by the phorbol ester PMA. In addition, the Vpr/Rip-1 nuclear translocation always preceded the accumulation of detectable extracellular virus by 24 hours. This functional correlation of nuclear translocation of the Vpr/Rip-1 complex and virus activation occurs despite the lack of a traditional nuclear localization signal.

It has been discovered that the Rip-1/Vpr complex associates with the activated GR type II receptor complex as part of the signalling pathway for Vpr. The Rip-1/Vpr/GR type II receptor complex translocates into the nucleus in the absence of steroid compounds normally associated with GR type II receptor translocation. It has been discovered that Rip-1 is associated with the GR type II receptor complex and that Rip-1 co-translocates into the nucleus together with GR type II receptor when GR type II receptor are induced to translocate as the result of binding to steroid compounds.

These discoveries provide a new target for the modulation of GR type II complex translocation. If GR type II complex translocation is desired, as in the case of diseases and conditions treated with steroids, Vpr, fragments of Vpr which bind to Rip-1, and Vpr-like compounds can be used to achieve the same result: GR type II complex translocation, in some cases without side effects associated with steroids. If prevention of GR type II complex translocation is desired, as in the case of diseases and conditions treated with glucocorticoid receptor antagonists, Rip-1-binding antagonists may be used to achieve the same result: prevention of GR type II complex translocation, in some cases without side effects associated with anti-glucocorticoids.

In some embodiments of the present invention, compounds are provided which act as non-steroidal therapeutics which mimic steroid activity. The non-steroidal therapeutics are useful in place of steroids. These compounds include Vpr and fragments thereof which induce GR type II complex translocation.

In some embodiments of the present invention, methods are provided which can be used to identify non-steroidal therapeutics which bind to Rip-1 and induce Rip-1/GR type II complex translocation. Such compounds can be used in place of steroids in the treatment of diseases and conditions in which steroid therapy is indicated.

In some embodiments of the present invention, compounds are provided which act as glucocorticoid antagonist-like therapeutics which mimic glucocorticoid antagonist activity but which bind to Rip-1 instead of GR. The Rip-1-binding-glucocorticoid antagonist-like therapeutics are useful in place of glucocorticoid antagonists. These compounds include proteins, peptides and other compounds which bind to Rip-1 but which do not induce GR type II complex translocation but rather inhibit such translocation.

In some embodiments of the present invention, methods are provided which can be used to identify glucocorticoid antagonist-like therapeutics which bind to Rip-1 but do not induce Rip-1/GR type II complex translocation but rather inhibit such translocation. Such compounds can be used in place of glucocorticoid antagonists in the treatment of diseases and conditions in which glucocorticoid antagonist therapy is indicated.

Experiments reported in Example 1 demonstrate that Vpr was able to induce the binding to the GRE sequences of the HIV-LTR, or the MMTV-LTR of the GR DNA-binding complex, as seen in a gel shift assay. In addition, Vpr was able to stimulate CAT activity from cells transfected with pGRE5/CAT, in the absence of other stimuli. Furthermore, the site of the HIV-1 LTR in which the GRE sequences where shown to lie is the same site to which the transactivation activity of both, Vpr and Dexamethasone mapped. These studies demonstrate that the HIV-1 vpr gene product mediates its functions in the viral lifecycle through a direct interaction with the glucocorticoid steroid biochemical pathway.

GR type II proteins are members of the ligand activated transcription factor superfamily of steroid hormone receptors. GR have been shown to act as powerful transactivators (Evans, 1988, The Steroid and Thyroid Hormone Receptor Superfamily. Science. 240, 889–895), involved in the proliferation and further differentiation of committed progenitor cells (Perrot-Applanat, et al., 1992, Immunolocalization of steroid hormone receptors in Normal and Tumour Cells: Mechanisms of their cellular traffic. Cancer Surv. 14, 5–30). GR type II are predominantly located in the cytoplasmic portion of resting cells (Madan and DeFranco, 1993, Bidirectional transport of glucocorticoid receptors across the nuclear envelope. Proc. Natl. Acad. Sci. USA. 90, 3588–3592; Lindenmeyer, et al., 1990, Glucocorticoid Receptor Monoclonal Antibodies Define the Biological Action of RU38486 in Intact 1316 Melanoma Cells. Cancer yes. 50, 7985–7991; Parker, 1992, Introduction; Growth Regulation by Nuclear Hormone Receptors. Cancer Surv. 14, 1–4), as part of a multi-protein complex, which is specifically formed by a GR molecule, a heat shock protein 90 dimer, and a heat shock protein 56 subunit.

When the steroid hormone binds its receptor, it promotes the transformation of these molecules to a less negatively charged DNA-binding form (Bodine and Litwack, 1990) The glucocorticoid receptor and its endogenous regulators. Receptor. 1, 83–120; Norman and Litwack, 1987, Hormones. (Orlando, Fla.: Academic Press, Inc.)). In addition, the composition of the activated GR complex is different from that of the resting complex. Heat shock protein 56 is shed, while heat shock protein 70 joins the other remaining members of this cluster. These activated complexes subsequently shuttle to the nuclear compartment (Newmeyer and Forbes, 1988 Nuclear import can be separated into distinct steps in vitro: nuclear pore binding and translocation. Cell. 52, 641–653; Richardson, et al., 1988, Nuclear protein migration involves two steps: rapid binding at the nuclear envelope followed by slower translocation through nuclear pores. Cell. 52, 655–664), where they bind specific nucleic acid sequences (Madan and DeFranco, 1993, supra; Perrot-Applanat, et al., 1992, supra).

Binding sites for GR are found in the HIV-LTR (Ghosh, 1992, Glucocorticoid Receptor Binding Site in the Human Immunodeficiency Virus Long Terminal Repeat. J. Virol. 66, 586–590; Katsanakis, et al., 1991, The human immunodeficiency virus long terminal repeat contains sequences showing partial homology to glucocorticoid response elements. Anticancer Res. 11, 381–383; Laurence, et al., 1990, Effect of glucocorticoids on chronic human immunodeficiency virus (HIV) infection and HIV promoter-mediated transcription. Blood. 74, 291–297; Miksicek, et al., 1986, Glucocorticoid responsiveness of the transcriptional enhancer of Moloney murine sarcoma virus. Cell. 46, 283–290). One such site is the TGTTCT (SEQ ID NO:1) GR target sequence found in the HIV LTR, homologous to that which has been defined for the MMTV LTR (Kolesnitchenko and Snart, 1992, Regulatory Elements in the Human Immunodeficiency Virus Type 1 Long Terminal Repeat LTR(HIV-1) Responsive to Steroid Hormone Stimulation. AIDS Res. Hum. Retrov. 8, 1977). Translocated GR type II complex recognizes and binds to GRE sequences of DNA that is located in the nucleus of cells. Binding of the GR type II complex to the GRE results in alteration of cellular activity and function.

The translocation effect of Vpr on Rip-1 as well as the transcriptional activation observed on the HIV-LTR, and the complementation in trans provided by Vpr protein for vpr mutant viruses was closely mimicked by two GR II stimulating steroids, Dexamethasone and Hydrocortisone. In addition, these three functions of Vpr could be inhibited with mifepristone, a GR II specific antagonist, which also curtailed the ability of Hydrocortisone and Dexamethasone to induce these effects. 9-cis retinoic acid, as well as all-trans retinoic acid were also tested for their influence on Rip-1 and other Vpr mediated functions.

The functional relationship between Vpr function and the glucocorticoid receptor transcriptional pathway is supported by several lines of evidence. Vpr and Rip-1 were co-immunoprecipitated with GR as part of the activated complex. In addition, Vpr stimulation induced the formation of the DNA (GRE)-binding forms of the GR complexes. Furthermore, Vpr was able to stimulate CAT expression from pGRE5/CAT, or alternatively from HIV LTR/CAT plasmids which contained the putative GRE sites (−250 to −264) within the LTR, yet failed to induce CAT expression in truncation mutants which lacked this site. Together, these data demonstrate that Vpr exerts its host cell altering effects through a direct interaction with the GR pathway, initially through the transcriptional activation of the LTR GRE sequences.

The nuclear translocation of the Vpr/Rip-1 complex is consistent with the observation that Vpr indirectly mediates the transactivation of the HIV-LTR. Very efficient HIV LTR-CAT induction by both the exogenous Vpr protein as well as by Vpr protein shed from neighboring cells was observed. The observation of nuclear co-translocation is also consistent with the observation that recombinant as well as serum-derived Vpr protein increases viral protein expression in newly infected as well as in latently infected cells, and in primary blood lymphocytes derived from an HIV positive individual.

The link between Vpr and the glucocorticoid receptor mediated transcriptional pathway establishes a link between a viral protein and several pathologies observed in AIDS patients. Glucocorticoids are have widespread immunosuppressive effects, and long term exposure of lymphocytes to glucocorticoids induces cell death. Furthermore, glucocorticoids also affect the lymphocytic precursors, providing the potential for a GR stimulating agent to accelerate the rate of thymic depletion and help, in part, to establish a state of general immune deficiency. These data are also interesting in light of the several observed pathological features which are present in some HIV-1 positive patients and also in some patients exhibiting glucocorticoid steroid toxicity. These common symptoms include muscle wasting and susceptibility to fungal infections. Furthermore these data suggest that the GR type II pathway could be exploited in an autocrine fashion by HIV through the action of the vpr gene product.

Compounds which have steroid-like activity can be identified and used in place of steroids. In particular, compounds such as Vpr and Rip-1-binding fragments of Vpr may be used as non-steroidal therapeutics. Such compounds can be used in place of standard steroid therapies, especially when the individual to be treated is experiencing or particularly susceptible to side effects linked to steroid use.

The discovery that Rip-1 associates with and co-translocates with GR type II complex can be used in methods of identifying compounds which mimic steroid activity or as inhibitors of GR translocation. Specifically, it has been discovered that Rip-1 is associated with the GR type II complex. When the GR type II complex is induced to translocate such as when it is bound to steroids, Rip-1, which is associated with GR type II complex is translocated into the nucleus together with the other components of the GR type II complex. Similarly, when Rip-1 is induced to translocate through Rip-1 binding to agents which bind to it and induce it to translocate, the GR type II complex is translocated into the nucleus together with Rip-1.

For example, Vpr protein binds to Rip-1 and results in the translocation of the GR type II complex, as well as Rip-1, from the cytoplasm to the nucleus. Thus, contact of cells with Vpr protein results in the biologically activity associated with GR type II translocation. Likewise, steroidal hormones which bind to GR cause the translocation of Rip-1 as well as the GR type II complex from the cytoplasm to the nucleus.

It has also been observed that compounds which inhibit translocation of the GR type II complex, inhibit translocation of Rip-1. Mifepristone, a glucocorticoid antagonist which inhibits translocation of GR inhibits Vpr activity.

In some embodiments, Rip-1 is used as a target for the identification and/or design of non-steroidal compounds which achieve the same effects of steroidal compounds, i.e. translocation of the GR into the nucleus and the biological effects associated with such translocation. Thus, methods of identifying compounds with steroid-like activity can be performed which comprise the steps of contacting cells that comprise Rip-1 and the GR type II complex with a test compound and measuring the level of Rip-1 and/or GR translocation into the nucleus.

The level of Rip-1 and/or GR translocation into the nucleus can be measured by a variety of means including physically identifying the presence and amount of Rip-1 and/or GR in the nucleus or cytoplasm in cells contacted with the test compound versus control assays in which the presence and amount of Rip-1 and/or GR in the nucleus or cytoplasm is measured in cells not contacted with the test compound. In some embodiments, test assays are performed in which cells that comprise Rip-1 and the GR type II complex are contacted with a test compound, a first positive control assay may be performed in which cells that comprise Rip-1 and the GR type II complex are contacted with a Vpr protein or a rip-binding fragment thereof, a second positive control assays may be performed in which cells that comprise Rip-1 and the GR type II complex are contacted with a steroids such as dexamethasone or hydrocortisone, a negative control assays may be performed in which cells that comprise Rip-1 and the GR type II complex are not contacted with rip-binding or steroid-based translocation activators. Some negative controls may comprise glucocorticoid receptor antagonist compounds such as, for example, mifepristone. The cells are then lysed and the nuclei are separated from the cytoplasmic fraction. Probes, such as anti-Rip-1 antibodies, anti-Vpr antibodies or anti-GR antibodies are used to identify and measure antigens present in the nuclei fraction and/or the cytosolic fraction. The positive controls will demonstrate that Rip-1 and GR translocate into the nuclei while the negative controls will show that absent a ligand to activate translocation, both Rip-1 and GR remain in the cytoplasm. The effectiveness of the test compound relative to the controls may be thus determined.

In other embodiments, the level of Rip-1 and GR translocation into the nucleus can be measured by a measuring the expression of marker genes which are only expressed upon translocation of the GR into the nucleus. Cells that comprise Rip-1 and GR type II complex are provided with gene constructs in which a marker gene is linked to a GRE. The cells are contacted with a test compound. Expression of the marker gene by the cells is specifically regulated by the translocation of GR from the cytoplasm into the nucleus. The cells are contacted with a test compound and if they then express the marker gene, induction of translocation is indicated. Positive controls which may be used include steroids, such as dexamethasone or hydrocortisone, which when contacted with the cells causes expression of the marker gene. Vpr may also be used as a positive control to bring about expression of the marker gene. Negative controls include compositions in which no Rip-1 or steroidal compounds are present or compositions which include glucocorticoid receptor antagonist compounds such as, for example, mifepristone. In negative controls, Rip-1/GR complex does not translocate and the cells do not express the marker gene.

In some embodiments, Rip-1 is used as a target for the identification and/or design of anti-steroidal compounds which achieve the same effects of glucocorticoid receptor antagonist compounds, i.e. prevent or inhibit the translocation of the GR into the nucleus and thus eliminate or reduce the biological effects associated with such translocation. Thus, methods of identifying compounds with anti-steroidal activity can be performed which comprise the steps of contacting cells that comprise Rip-1 and GR with a test compound and determining the level of Rip-1 and/or GR translocation into the nucleus. The level of Rip-1 and/or GR translocation into the nucleus can be measured by the same means as those described above. In the case of identifying compounds which induce the same results as glucocorticoid receptor antagonists, the positive controls include known glucocorticoid receptor antagonist compounds such as, for example, mifepristone. The test assays may be performed as set out above in which translocation is assessed by identifying Rip-1 and/or GR in the nuclear and/or cytoplasmic fractions of lysed and separated cells or by measuring gene construct expression in cells that have a marker gene under the control of regulatory elements that include GRE sequences.

The methods for identifying Rip-1 binding compounds which act as non-steroidal therapeutics that mimic either steroid activity or glucocorticoid receptor activity can be performed routinely. Cells which contain both Rip-1 and GR are readily available and described in Example 1. Test compounds may be added to such cells to determine if the test compound induces the Rip-1/GR complex to translocates from the cytoplasm to the nucleus. Methods of determining whether translocation has occurred and the level of translocation can be performed routinely.

Cells contacted with compounds are incubated for a sufficient period of time and under suitable conditions to allow for translocation. Such conditions are well to those having ordinary skill in the art and are essentially those conditions in which Vpr protein or steroids such as dexamethasone or hydrocortisone will induce translocation of the Rip-1 and GR type II complex. Generally, cells are incubated with test compounds for 30 minutes to 24 hours.

In the embodiments in which the level of translocation is measured by comparing nuclear to cytosolic fractions of cells exposed to test compound to the level measured or expected in positive and negative controls, the cells are lysed and fractions which contain the nuclei are separated from fractions which contain the cytoplasm. Cells can be lysed by any one of several well known means such as chemical lysis using detergents for example, sonication, mechanical disruption or combination thereof. Centrifugation of lysed cellular material to pellet nuclei while maintaining cytoplasmic contents in solution is well known. Techniques for separating nuclei from cytoplasm are described in Zwerner, et al. 1979 Cell Culture, Eds. Jakoby and Pastan, Ch. 18, pps 221–229 (Methods in Enzymology vol. 58) Academic Press, San Diego, Calif., which is incorporated herein by reference.

The amount of either Rip-1 or GR or both may be measured in either the nuclei fraction or the cytosolic fraction or both. It is also contemplated that in addition to Rip-1 and GR, the presence and amount of other components of the GR type II complex may be measured in the nuclear fraction to determine translocation. The presence and amount of Rip-1 or GR may be measured by standard ELISA assay. Results can be compared with those observed in control assays using known inducers of translocations such as Vpr protein or steroids such as hydrocortisone and dexamethasone, and known inhibitors of translocations such as glucocorticoid receptor antagonists including mifepristone. These data can be used to determine whether translocation was induced or inhibited and the level of such induction or translocation.

The presence of Rip-1 or GR may be identified in the nuclear fraction to detect translocation. Further, the level of Rip-1 or GR in the cytosolic fraction may be measured to indicate translocation. It is also contemplated that the presence of the heat shock protein 90 dimer, the heat shock protein 70 subunit or Vpr or a Rip-1 binding protein/peptide may be identified in the nuclear fraction to measure translocation. The detection of any of the proteins in cellular fractions can be performed routinely using antibodies against the proteins to be detected, i.e. antigens. One having ordinary skill in the art can detect antigens using well known methods. One having ordinary skill in the art can readily appreciate the multitude of ways to practice a binding assay to detect antigens in either the nuclear or cytoplasmic fraction. For example, antibodies are useful for immunoassays to detect antigens. The immunoassay typically comprises incubating the fraction with a detectably labeled high affinity antibody capable of selectively binding to the antigen, and detecting the labeled antibody which is bound to the protein. Various immunoassay procedures are described in *Immunoassays for the 80's*, A. Voller et al., Eds., University Park, 1981, which is incorporated herein by reference.

In this aspect of the invention, the antibody or the fraction which may contain the antigen may be added to nitrocellulose, or other solid support which is capable of immobilizing proteins. The support may then be washed with suitable buffers followed by treatment with the detectably labeled antigen-specific antibody. The solid phase support may then be washed with the buffer a second time to remove unbound antibody. The amount of bound label on said solid support may then be detected by conventional means.

By "solid phase support" or "carrier" is intended any support capable of binding antigen or antibodies. Well-known supports or carriers, include glass, polystyrene, polypropylene, polyethylene, dextran, nylon, amylases, natural and modified cellulose, polyacrylamide, agarose, and magnetite. The nature of the carrier can be either soluble to some extent or insoluble for the purposes of the present invention. The support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of antibodies may be determined according to well known methods. Those skilled in the art will be able to determine operative and optimal assay conditions for each determination by employing routine experimentation. Antibodies that bind to the targeted antigens may be detectably labelled. Alternatively, antibodies that bind to the antibodies that bind to the targeted antigens may be detectably labelled.

One of the ways in which the antibodies can be detectably labeled is by linking the same to an enzyme and use in an enzyme immunoassay (EIA), or enzyme-linked immunosorbent assay (ELISA). This enzyme, when subsequently exposed to its substrate, will react with the substrate generating a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the antibody, it is possible to detect it through the use of a radioimmunoassay (RIA) (see, for example, Work, T. S., et al., *Laboratory Techniques and Biochemistry in Molecular Biology*, North Holland Publishing Company, N.Y., 1978, which is incorporated herein by reference). The radioactive isotope can be detected by such means as the use of a gamma counter or a scintillation counter or by autoradiography. Isotopes which are particularly useful for the purpose of the present invention are: $^3$H, $^{125}$I, $^{131}$I, $^{35}$S, $^{14}$C, and, preferably, $^{125}$I.

It is also possible to label the antibody with a fluorescent compound. When the fluorescent labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence-emitting metals such as $^{152}$Eu, or others of the lanthanide series. These metals can be attached to the TNF-specific antibody using such metal chelating groups as diethylenetriaminepentaacetic acid (DTPA) or ethylenediaminetetraacetic acid (EDTA).

The antibody also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. Detection of the Vpr-specific antibody or the antibody that binds to the Vpr receptor protein may be accomplished by a scintillation counter, for example, if the detectable label is a radioactive gamma emitter, or by a fluorometer, for example, if the label is a fluorescent material.

In the case of an enzyme label, the detection can be accomplished by colorometric methods which employ a substrate for the enzyme. Detection may also be accomplished by visual comparison of the extent of enzymatic reaction of a substrate in comparison with similarly prepared standards.

The components of the assay may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Assays which can be adapted for the present invention are described by Wide, *Radioimmune Assay Method*, Kirkham, Ed., E. & S. Livingstone, Edinburgh, 1970, pp. 199-206 which is incorporated herein by reference.

In some embodiments, an antibody is fixed to a solid phase. Samples which may or may not contain antigen are contacted with the fixed antibody to form a complex. The complex is contacted with a second antibody. The solid phase is washed to removed unbound material. Detection of the second antibodies that the antigen is present in the sample.

A further aspect of the present invention relates to kits for practicing the above described method of identifying compounds which induce or inhibit Rip-1/GR type II complex translocation. Kits according to this aspect of the invention comprises the a first container comprising isolated antigen such as Rip-1 or GR, a second container comprising antibodies that specifically bind to the antigen. The antibodies are used in the immunoassay and the antigen are the positive control. In one such embodiment of this aspect of the invention, the antibody is labelled. In another embodiment of this aspect of the invention, a third container comprising a labelled antibody that specifically binds to anti-antigen antibody is provided.

In other aspects of the invention, the antibodies described above are used in well known Western blot techniques to identify antigens in nuclear or cytoplasm fractions. SDS PAGE is used to further separate the components of the nuclear and/or cytoplasmic fractions. The gels are then contacted with a solid carrier such as nitrocellulose paper to transfer the protein thereon. The paper is then probed with the antibodies. Western blots are described in Sambrook et al., *Molecular Cloning a Laboratory Manual*, Second Ed. Cold Spring Harbor Press (1989) which is incorporated herein by reference.

In some embodiments, GR translocation may be determined and measured by introducing into the cells a gene construct which comprises a marker gene whose expression is under the regulatory control of a promoter with a glucocorticoid response element (GRE) which is a nucleotide sequence. When GR is bound to the GRE, expression of the marker gene occurs. Thus if translocation occurs, the marker gene will be expressed and is translocation does not occur, no expression of the marker gene will occur. Promoters with GREs are well known. Examples of promoters with GRE include the HIV LTR and MMTV LTR. Marker genes are well known and generally encode detectable proteins normally not found in the cells where the marker is being used. Examples of common marker genes include the bacterial enzymes chloramphenicol transferase (CAT) and beta galactosidase. CAT os particularly useful since a routine enzyme assay is available which can readily quantify the amount of CAT present and thus the level of expression of the marker gene. The level of expression is indicative of the level of translocation. Example 1 describes examples of gene constructs useful in the present invention. Results can be compared with those observed in control assays using known inducers of translocations such as Vpr protein or steroids such as hydrocortisone and dexamethasone, and known inhibitors of translocations such as glucocorticoid receptor antagonists including mifepristone. These data can be used to determine whether translocation was induced or inhibited and the level of such induction or translocation.

According to another aspect of the present invention, methods of evaluating the level of infection of individuals infected with human immunodeficiency virus (HIV) are provided. The discovery that Vpr induces translocation of the GR type II complex allows for assays in which samples from an infected individual may be assayed in a translocation assay, particularly those assays in which a marker gene is expressed when cells are contacted with Vpr. Infected individuals have Vpr in body fluids. Samples of body fluid may be assayed to detect and quantify Vpr in the sample as an diagnostic for HIV and as a prognosticator of the progress of infection. Vpr titers increase with progression of HIV infection. The translocation assays described herein provide a means to quantify the level of Vpr in an infected individual and thereby monitor the progress of infection.

Test samples include those samples that are obtained from individuals suspected of being HIV+ and may consist of blood, cerebral spinal fluid, amniotic fluid, lymph, semen, vaginal fluid or other body fluids. Test samples also include those samples prepared in the laboratory, such as those used for research purposes. Cells, if present, may be removed by methods such as centrifugation or lysis. One skilled in the art would readily appreciate the variety of test samples that may be examined for Vpr. Test samples may be obtained by such methods as withdrawing fluid with a needle or by a swab. One skilled in the art would readily recognize other methods of obtaining test samples.

The translocation assays described herein may be used to detect and quantify Vpr in a sample. The most convenient assay described herein is the use of cells that contain Rip-1 and GR type II complex which have been transfected with a gene construct comprising a marker gene under the control of regulatory sequences that include a GRE. Such assays are described herein. The assays are used to detect and measure Vpr in a sample by contacted the cells with the sample and quantifying the amount of marker gene expressed. Controls include compositions that contain known amounts of Vpr.

Kits contain a container with the gene construct and a second container that has known quantities of Vpr at a known concentration. In some kits, the gene construct is incorporated with cells.

Another aspect of the present invention relates to the use of Vpr protein or Rip-1-binding fragments of Vpr protein useful as transfection agent, particularly for the delivery of nucleic acid molecules or derivatives thereof into the nucleus of a cell. Nucleic acid molecules may be conjugated to Vpr or Rip-1-binding fragments thereof in order to facilitate entry of the nucleic acid molecule into the nucleus.

As disclosed herein, Vpr translocates into nucleus of cells when it binds to Rip-1. Thus, agents whose presence in the nucleus is desirable may be conjugated to Vpr or fragments thereof in order to facilitate entry of such agents into the nucleus.

In some embodiments, nucleic acid molecules are conjugated to Vpr or fragments thereof. Such conjugated nucleic acid molecules are efficiently transported into the nucleus. In some embodiments, the nucleic acid molecule is a gene construct which comprises a coding sequence operably linked to regulatory elements which direct expression of the coding sequence. In some embodiments, the nucleic acid molecule is an antisense molecule or a coding sequence of an antisense molecule or a ribozyme or a coding sequence for a ribozyme. Incorporation of such molecules into the nucleus, inhibits expression of endogenous genes whose expression or overexpression is undesirable.

In some embodiments of the invention, nucleic acid molecules such as DNA are conjugated to Vpr or fragments of Vpr which bind to Rip-1 and which when bound to Rip-1 induce translocation. The nucleic acid molecule may be conjugated to the Vpr protein or fragment thereof by well known cross linking techniques and agents such as homobifunctional succinimidyl esters, preferably with carbon chain spacers such as disuccinimidyl suberate (Pierce Co, Rockford, Ill.). In the event that a cleavable conjugated compound is required, the same protocol would be employed utilizing 3,3'-dithiobis (sulfosuccinimidylpropionate; Pierce Co.). Other crosslinker include sulfoMBS and sulfaldehyde.

In some embodiments of the invention, active agents such as drugs and radioisotopes are conjugated to Vpr or fragments of Vpr which bind to Rip-1 and which when bound to Rip-1 induce translocation. The small molecules may be conjugated to the Vpr protein or fragment thereof by well known cross linking techniques and agents homobifunctional succinimidyl esters, preferably with carbon chain spacers such as disuccinimidyl suberate (Pierce Co, Rockford, Ill.). In the event that a cleavable conjugated compound is required, the same protocol would be employed utilizing 3,3'-dithiobis (sulfosuccinimidylpropionate; Pierce Co.). Other crosslinker include sulfoMBS and sulfaldehyde.

In some embodiments of the invention, active agents such as protein based toxins are conjugated to Vpr or fragments of Vpr which bind to Rip-1 and which when bound to Rip-1 induce translocation. The toxins may be conjugated to the Vpr protein or fragment thereof by well known cross linking techniques and agents such as disuccinimidyl suberate, 3,3'-dithiobis (sulfosuccinimidylpropionate; Pierce Co.), by disulfide bonds between cysteine residues in separate protein molecules to form dimers or by constructing a chimeric gene that encodes a fusion protein which comprises a Vpr derived portion and a toxin portion. Those having ordinary skill in the art can readily design dimers crosslinked with crosslinking agents or disulfide bonds or generate and express chimeric genes that encode fusion proteins.

The conjugated compositions and fusion proteins of the present invention may be used to deliver active agents to the nucleus of cells in both in vitro and in vivo protocols. As discussed above, active agents include nucleic acid molecules, drugs, radioisotopes, and toxins for example. In some embodiments, the active agent is selected from the group consisting of: methotrexate, doxorubicin, daunorubicin, cytosinarabinoside, etoposide, 5-4 fluorouracil, melphalan, chlorambucil, cis-platinum, vindesine, mitomycin, bleomycin, purothionin, macromomycin, 1,4-benzoquinone derivatives, trenimon, ricin, ricin A chain, Pseudomonas exotoxin, diphtheria toxin, *Clostridium perfringens* phospholipase C, bovine pancreatic ribonuclease, pokeweed antiviral protein, abrin, abrin A chain, cobra venom factor, gelonin, saporin, modeccin, viscumin, volkensin, alkaline phosphatase, nitroimidazole, metronidazole and misonidazole. Such active agents are conjugated to Vpr or fragments of Vpr that bind to Rip-1 and induce translocation of Rip-1 to the nucleus. Vpr may be isolated from natural sources or produced by a variety of well known means such as those described in U.S. Ser. No. 08/019,601 filed Feb. 19, 1993 and U.S. Ser. No. 08/167,608 filed Dec. 15, 1993, both of which are incorporated herein by reference. Fragments of Vpr that bind to Rip-1 and induce translocation of Rip-1 to the nucleus are fragments of Vpr as described herein, particularly Example 3, and may be identified as described herein.

Conjugated compositions may be targeted to cells by further linking cell specific receptor binding peptides to the conjugated composition or encapsulating the conjugated composition within a vector such as a liposome, a viral particle or a viral package.

According to another aspect of the invention, Vpr or fragments of Vpr that bind to Rip-1 can be used to identify the presence and location of GR type II complex in cells and cellular material that comprises Rip-1 and GR type II complex. It has been discovered that Vpr binds to Rip-1 and Rip-1 binds to GR type II complex. Thus, in protocols in which the location within a cell of GR type II complex is to e determined, Vpr or a Rip-1-binding fragment thereof can be used. Vpr or a fragment thereof may be labelled or detected using detectable antibodies that bind to the Vpr and fragment thereof. The detectable antibodies may be labelled or targeted with labelled anti-antibody antibodies or ligands that bind to the Fc portion of the antibody. Protocol for locating GR type II complex within a cell include those in which compounds are screened which are being tested for their ability to bind to GR and either induce or inhibit GR type II translocation. Isolated Vpr or fragments thereof, particularly that which is produced in eukaryotic cells such as baculovirus produced Vpr is therefore useful and a detectable ligand for both Rip-1 and for detecting GR type II complex.

EXAMPLES

Example 1

METHODS

Ligand blot $3 \times 10^6$ cells were washed twice in PBS, and lysed in 200 µl of lysis buffer (150 mM NaCl, 50 mM Tris, pH 8.0, 0.5% Triton X-100, plus protease inhibitors: aprotinin, leupeptin, pepstatin A, each at 2 µg/ml; PMSF, 1 mM, and EDTA, 1 mM). Cell suspension was incubated on ice for 10 minutes with frequent vortexing, and centrifuged at 12000 g for 6 minutes. The soluble, as well as the insoluble fractions were run on 12% SDS-PAGE, and transferred to PVDF membranes (Millipore), as described. Membranes were blocked with 5% non fat dry milk, in TBS supplemented with 0.05% Tween-20. Blocked membranes were incubated with either purified Vpr protein (approximately 50 ng/ml) or an irrelevant protein. These membranes were then incubated with 808 rabbit anti Vpr antiserum Levy, et al. 1994b, supra, followed by $I^{125}$ protein G (NEN), and exposed to film for at least 12 hours at −80° C.

Construction of the Vpr-CNBr-Sepharose column

This column was constructed by coupling purified recombinant Vpr to cyanogen bromide activated sepharose beads (Sigma). Recombinant Vpr at 1 mg/ml was incubated with swelled beads for 2 hours at 25° C. in 10 mM NaHCO₃, 0.5M NaCl, pH 8.3. The coupled beads were blocked with 1M glycine. After loading the column with antigen, elution was performed using first pre-elution buffer composed of 10 mM Sodium Phosphate, pH 6.8, followed by elution buffer consisting of 100 mM glycine, pH 2.5. Elution fractions were neutralized with 1/20 volume 1M sodium phosphate, pH 8.0.

Cell culture and virus preparation

The following cell lines were obtained from the American Type Culture Collection; TE671 human embryonal rhabdomyosarcoma (ATCC HTB139), A673 embryonal rhabdomyosarcoma (ATCC CRL 1598), D17 canine osteosarcoma (ATCC CCL183), HOS human osteosarcoma (ATCC CRL 1543), U373 human glioblastoma (ATCC HTB17), SK-N-MC neuroblastoma (ATCC HTB10). Two additional glioblastoma lines were kindly provided by the Medical Research Council (MRC), England, (HT17 and HT16). U87MG (HTB14) is a glial cell line obtained from the University of Pennsylvania Cell Center. RD rhabdomyosarcoma cells were provided by Dr. A. Srinivasan. The T lymphocytic cells H9 and SupT-I were obtained from the University of Pennsylvania Cell Center, and KG-1 was obtained from Dr. G. Trinchieri. The murine NIH 3T3 line was obtained from ATCC. BSC-1, CV-1 and COS cell lines were obtained Dr. B. Moss. Primary PBL as well as primary monocytes/macrophages were isolated as in Levy, et al. 1994b, supra. All non-hematopoietic cells were cultured in DMEM with 10% heat inactivated fetal calf serum, penicillin/streptomycin, I-glutamine, Hepes (25 mM) and sodium pyruvate. Hematopoietic cells were cultured in RPMI 1640 as above except using 10% autologous human serum. Virus were prepared as described in Levy, et al., 1994b, supra; Levy, et al., 1994a, supra, which are incorporated herein by reference.

Antibodies

The rabbit anti-Vpr peptide serum (aa 2-21, "808") was obtained from Bryan Cullen through the NIH ARRRP. The human anti-Gag p24 (V7.8) was obtained from Ronald Kennedy through the NIH ARRRP. The sheep anti-p24 was obtained from the FDA through the NIH ARRRP. Capture ELISA for Gag p24 antigen was performed as previously reported (Levy, et al. 1994b, supra; Koenig, et al., 1986, Detection of AIDS virus in macrophages in brain tissue from AIDS patients with encephalopathy. Science, 233, 1089–1093).

Crosslinking of the Vpr/Rip-1 complexes

Fractions containing eluted Vpr/Rip-1 complexes were pooled and dialyzed against three changes of water, the lyophilized and resuspended in PBS to a tenth of the original volume. This material was then exposed to either the non-cleavable agent, DSS, or the cleavable crosslinking agent, DTSSP (Pierce), 50 mg/ml in 50% DMSO, 50% H₂O vol/vol. Conditions used as in Weiner, 1989, A point mutation in the neu oncogene mimics ligand induction. Nature, 339, 230–231, which is incorporated herein by reference.

Expression and purification of recombinant HIV-1 Vpr

The expression of Vpr in insect cells has been described in Refaeli, et al., 1993, Expression of biologically active recombinant HIV-1 Vpr protein from baculovirus. (Submitted), which is incorporated herein by reference. Briefly, the vpr open reading frame from HIV-1 NL43 was cloned into the baculovirus expression vector pVL1393 and this construct was co-transfected with linearized DNA from Autograph California nuclear polyhidrosis virus (Baculogold-AcMNPV) into Spodoptera frugipera (Sf-9) cells. The resulting recombinant baculoviruses were plaque purified and expanded following well known protocols (O'Reilly, et al., 1992, Baculovirus expression vectors: a laboratory manual. (New York: W. N. Freeman)). For protein expression, Nigh five cells were infected at 5–10 MOI, at a cell density of $2 \times 10^6$ cell/ml. The tissue culture supernatants were harvested 24 hours later were then centrifuged at 10,000 G. These supernatants were supplemented with protease inhibitors (PMSF, EDTA, EGTA, aprotinin, pepstatin A, and Leupeptin), dialyzed against PBS, then filtered sterilized and kept on ice until used. Control supernatants consisted of baculovirus supernatants prepared as above from cells infected with recombinant baculoviruses lacking a gene insert.

For purification, Triton X-100 at 0.05% final concentration was added to the baculovirus, supernatants, then the supernatants were passed over a rabbit anti-Vpr column constructed following published protocols (Harlow and Lane, 1988, Antibodies: A laboratory manual. (Cold Spring Harbor, NY: Cold Spring Harbor Laboratory Press), which is incorporated herein by reference). After extensive washing with PBS, 0.05% Triton X-100, the columns were eluted as follows. Three bed volumes of a pre-elution buffer of 10 mM Phosphate buffer plus Triton X-100 (0.05%), pH 8.0, were passed through the column, followed by the elution buffer consisting of 10 mM Triethanolamine plus 0.05% Triton X-100, pH 11.5. The eluate was collected in 0.5 ml aliquot and neutralized with 1/20 volume of 1M sodium phosphate buffer, pH 6.8.

The immunoaffinity columns were constructed by coupling the indicated antibody to protein G beads using Dimethyl pimelimidate-2-HCL (DMP) (Pierce). The Vpr column was constructed by coupling purified recombinant Vpr to cyanogen bromide activated sepharose beads (sigma). Recombinant Vpr at 1 mg/ml was incubated with swelled beads for 2 hours at 25° C. in 100 mM $NaHCO_3$, 0.5M NaCl, pH 8.3. The coupled beads were blocked with 1M glycine. After loading the column with antigen, elution was performed using first pre-elution buffer composed of 10 mM sodium phosphate, pH 6.8, followed by elution buffer consisting of 100 mM glycine, pH 2.5. Elution fractions were neutralized with 1/20 volume 1M sodium phosphate, pH 8.0. LTR-CAT assays.

Induction of the HIV-LTR was measured as a function of a reporter gene (CAT) function. pBennCAT, an LTR-CAT encoding construct, obtained from M. Martin, through the NIH ARRRP was used. The levels of CAT protein were measured using a CAT ELISA capture assay (Boehringer Mannheim), following manufacturer's specifications. The levels of CAT activity were measured by a chloramphenicol acetyltransferase assay, according to published procedures (Gorman, et al., 1982, The Rous sarcoma virus long terminal repeat is a strong promoter when introduced into a variety of eukaryotic cells by DNA mediated transfection. Proc. Natl. Acad. Sci. USA. 79, 6777–6781). Briefly, RD cells were transfected with pBennCAT (Gendelman, 1986, Transactivation of the Human immunodeficiency virus long terminal repeat sequence by DNA viruses. Proc. Natl. Acad. Sci. USA. 83, 9759–9763), using DOTAP. Cells were washed 12 hours later and new medium, containing the test reagents was added to the cell monolayers. 48 hours later, cells were washed three times with Ca+2/Mg+2 free PBS. Cells were then scraped off the plate, and collected with 1 ml PBS. Cell pellets were lysed by resuspending them in 100 μl 0.25M Tris, pH 7.8, and undergoing three freeze-thaw cycles using an ethanol-dry ice bath, and a 37° C. water bath. Lysates were spun at 12,000 G for 5 minutes and samples were stored at −20° C. until they were used. The CAT reaction was set up using 5 μl $C^{14}$ chloramphenicol (40–50 mCi/mmole), 70 μl $ddH_2O$, 35 μl 1M Tris, pH 7.8, 20 μl 4 mM acetyl Coa (Pharmacia), 20 μl cell lysate. The reactions were incubated at 37° C. for an hour, and subsequently extracted with 1 ml ethyl acetate. After resuspension in 20 μl ethyl acetate, samples were spotted on the silica gel TLC plates (Whatman), and developed in chloroform:methanol (95:5); ascending. Gels were dried and exposed to film (Kodak XAR) overnight at room temperature. The panel of HIV-1 LTR/CAT mutants were obtained from Dr. Joseph Stevens, through the NIH ARRRP. pGRE5/CAT was obtained from United States Biochemicals.

Immunoprecipitation of GR complexes

U937 myeloid cells were stimulated with the studied agents, and exposed to crosslinking agents (DSS or DTSSP accordingly) and subsequently lysed with the lysis buffer described earlier. These lysates were spun at 12000 g for 10 minutes, and immediately used for immunoprecipitation procedures which were done as previously described. The antibody used in these immunoprecipitations was a mouse anti-human GR (Affinity bioreagents). Alternatively, resting U937 cells were lysed as described above, and supplemented with the studied agents. The stimulated lysates were then exposed to crosslinking agents, and these preps used for immunoprecipitation procedures.

All the resulting fractions were subsequently used for SDS-PAGE, western blot, or a Vpr-ligand blot for the detection of Rip-1. The antibodies used were 808 (rabbit anti-Vpr), and the mouse anti-GR antibody, which was used to precipitate these complexes.

Gel shift assays

U937 cells were lysed by swelling on ice, with constant vortexing, for 15 minutes with 0.075M KCl, supplemented with PMSF, Aprotinin, Leupeptin A and pepstatin. These lysates were spun at 12000 g for 10 minutes and kept on ice until used. These cell lysates were stimulated with Vpr protein, a control (pVL), Dexamethasone, or 9-cis-Retinoic Acid. The binding buffer used was 12% glycerol, 12 mM HEPES (pH 7.9), 4 mM Tris (pH 7.9), 60 mM KCl, 1 mM EDTA, and 1 mM DTT. The oligonucleotides sequences used were obtained from D. Ghosh.

The HIV-1/2 (32)P labelled probe was prepared by annealing an HIV-1 oligonucleotide (GATCCGGCCCAA-TAAAGGAGAGAACACCAGCTTGTTACACCCTGTG-AG-SEQ ID NO:2) and HIV-2 nucleotide (GATCCTCA-CAGGGTGTAACAAGCTGGTGTTCTGTCCTTTATTG-GCCG-SEQ ID NO:3), followed by filling the resulting BamHI site with Klenow enzyme. The radiolabelled synthetic probe and the stimulated cell lysates were incubated with 100 molar excess of the unlabelled MMTV GRE probe, or with an unlabelled, unrelated (polyoma virus EF-C) recognition sequence-containing oligonucleotide in a competitive gel shift assay. The competitors were prepared by annealing single stranded oligonucleotides GRE1 (GATCCGTTTATGGTTACAAACTGTTCTTAAAACA-AG-SEQ ID NO:4) and GRE2 (GATCCTTGTTTTAAGA-ACAGTTTGTAACCATAAACG-SEQ ID NO:5) and the unrelated EF-C oligonucleotides, EF-C1 (GATCCATTAGTTGCTAGGCAACTGGCG-SEQ ID NO:6) and EF-C2 (GATCCGCCAGTTGCCTAGCAACTAATG-SEQ ID NO:7). The oligonucleotides were annealed by heating up to 80° C., for 15 minutes, and letting cool down at room temperature. The protein-DNA mixtures were incubated in the binding buffer described, for 30 minutes at room temperature. All samples were subsequently ran on a nonreducing, non-denaturing polyacrylamide gel (270 μl 1M Tris, pH 7.9; 80 μl 0.5M EDTA, pH 7.9; 13.2 μl 1M sodium acetate, pH 7.9; 5.33 ml 30% Acrylamide; 1 ml 2% bisacrylamide, 2 ml 50% glycerol, 31 ml ddH2O), using a low ionic strength buffer (26.9 ml 1M Tris, pH 7.9; 13.2 ml 1M sodium Acetate, pH 7.9; 8 ml 0.5M EDTA, pH 8.0; up to a final volume of 4 liters with ddH2O). Gels were run at 30–35 mA, until the Bromophenol Blue had migrated ¾ of the length of the gel. Gels were dried on Whatman paper, and exposed to Kodak X-AR film for periods spanning from 6 hours to 7 days.

RESULTS

Expression of Vpr in insect cells

To construct a recombinant baculovirus containing the vpr gene, the vpr open reading frame was subcloned from the vpr-pBabepuro expression plasmid, which has been previously described (Levy, et al., 1993, supra, which is incorporated herein by reference), into the multiple cloning site of pVL1393 baculovirus expression vector (Invitrogen) downstream of the baculovirus polyhedron promoter. This construct is predicted to encode a non-fused, native Vpr protein (Levy, et al, 1994a, supra). Co-transfection of this plasmid along with linearized AcMNPV genomic DNA (Baculogold, PharMingen) into Sf-9 (Spodoptera frugiptera) insect cells yielded recombinant baculoviruses containing the vpr gene. Twenty four hours after transfection, virus-containing supernatants from transfected cells were applied to Nigh-five cells (Tricholupisa ni) whose supernatants and cell fractions were then assayed for Vpr protein expression. The recombinant Vpr protein obtained was identical in its apparent molecular weight and seroreactivity to the native, viral borne protein. When added to the culture media of rhabdomyosarcoma cells (RD), this protein induced growth arrest and cellular differentiation in a manner similar to that which was obtained by transfection of the vpr gene, HIV-1 genomic DNA, or by infection with HIV-1.

Identification of Vpr cellular binding proteins in cell lysates

In order to further characterize the biochemical aspects of Vpr activity on cells, the interaction of Vpr with cellular proteins which might couple Vpr to intracellular signaling pathways was investigated. Cell lysates from $3\times10^6$ RD cells were obtained using either Triton X-100, SDS, or Sodium Deoxycholic acid. Following SDS-PAGE of the Triton X-100 soluble and insoluble fractions as well as those of the SDS and sodium deoxycholic acid lysates, proteins were transferred to membranes and probed with recombinant Vpr (Vpr-ligand blot). A single 41 Kd protein (Rip-1) was detected from each of the soluble fractions and not in the Triton X-100 insoluble fraction. Rip-1 was detected by using either the recombinant or virally derived Vpr proteins. In addition, Rip-1 and Vpr coeluted from a Vpr specific immunoaffinity column. Next, a Vpr-CNBr activated Sepharose column loaded with the Triton X-100 soluble fraction of RD cell lysates was eluted at pH 2.5, to yield essentially a single protein band (>95% purity). This protein matched in size to Rip-1, and reacted with Vpr in a ligand blot system in a manner identical to the protein found in total cell lysate. Furthermore, Rip-1 and Vpr could be reversibly crosslinked to a 58 Kd heterodimeric complex that reacted with the Vpr specific antibody in western blots, and in Vpr ligand blots. Therefore Rip-1 likely represents a cellular target for Vpr.

Rip-1 was detected in both rhabdomyosarcoma (RD cells) and U937 cells of the myeloid lineage. In addition, Rip-1 was found to be present in cell lines derived from a variety of tissues, including several cell lines of T lymphoid (H9 and SupT1) and myeloid origin (U937, HL60, KG-1, THP-1), as well as in other rhabdomyosarcoma (TE671, A673), osteosarcoma (HOS, D17), astrocytoma (HT017, HTB14, HT16, HT17) and neuroblastoma (HTB10) cell lines. Rip-1 was also detected in primary lymphocytes and in adherent monocyte/macrophage cells obtained from a healthy HIV-1 seronegative donor. Rip-1 is present in cell lineages which are the primary targets of HIV infection. Rip-1 was not detected however in murine NIH-3T3 cells, nor in CV-1, BSC-1, or COS cells. Interestingly, these four cell lines have been reported to lack endogenous GR (Madan and DeFranco, 1993, supra; Picard and Yamamoto, 1987. Two signals mediate hormone-dependent nuclear localization, of the glucocorticoid receptor. EMBO. 6(11), 3333–3340). The expression of Rip-1 in a diverse collection of transformed and untransformed cell types may suggest that Rip-1 is part of a basic cellular pathway linked to cellular proliferation and differentiation.

Cellular trafficking studies of Rip-1 in response to Vpr and other stimuli

The cellular localization of Rip-1 was determined through cellular fractionation studies. Vpr protein did not appear to bind to the cell surface of SupT1, RD, or HL60 cells as determined by an indirect fluorescence assay. In additional studies the nuclear components were segregated from the cytosolic and membrane bound elements of the cell utilizing a Triton X-100 lysis procedure. Rip-1 was found to be consistently present in the cytosolic fraction of cells prior to Vpr exposure.

Upon exposure of such cells to Vpr protein, or HIV-1 virus, but not to the phorbol ester PMA, Rip-1 was observed to translocate from the cytoplasmic to the nuclear fraction. Similarly an infectious vpr deletion mutant HIV-1 virus (HIV-1 NL43 Δvpr) (Levy, et al., 1993), could not induce Rip-1 translocation following infection of U937 cells. Importantly, Vpr was observed to co-translocate to the nucleus with Rip-1, as assessed by Vpr-ligand blot assays.

The characteristics of the viral replication kinetics could also be correlated to the location of Rip-1 in the cell. U937 cells which were infected with HIV-1 NL43 were found to produce detectable levels of virus at day 4 post infection. Rip-1 was observed to co-translocate to the nucleus with Vpr on day 3 post infection.

U937 cells which were infected with HIV-1 NL43 Δvpr failed to establish a productive infection. Such nonproductively infected cells can be rescued for p24 production by addition of exogenous Vpr protein (Levy, et al., 1994a, supra; Levy, et al., 1994b, supra). Exogenous Vpr protein induced the nuclear translocation of Rip-1 by 12 hours after the initial exposure of the cells. When the nonproductively infected U937 cells described above were exposed to Vpr protein, Rip-1 translocated 12 hours later, and virus was first detected in the media 36 hours after the initial exposure to Vpr. Such correlative data provides further evidence for the coupling of functions of Vpr and Rip-1 in the HIV infection process.

Nuclear translocation of Rip-1 is induced by Hydrocortisone and Dexamethasone, in the absence of Vpr It is possible that Rip-1 is a carrier protein which translocates Vpr to the cell nucleus where Vpr could exert its biological function. Alternatively, Vpr could function as the ligand for a protein involved in a distinct cellular signalling pathway. Along these lines, the cellular trafficking characteristics observed for Rip-1 are characteristic in many ways to members of the glucocorticosteroid receptor superfamily (reviewed in Evans, 1988, supra; Parker, 1992, supra; Beato, 1989, Gene regulation by steroid hormones. Cell. 56, 335–344; Green and Chambon, 1988, Nuclear receptors enhance our understanding of transcription regulation. Trends. Genet. 4, 309–314) or translocation/transcription complex. Type II glucocorticoid receptors (GR) and their accessory proteins in particular translocate from the cytoplasm to the nucleus upon binding to their ligand. GR have been shown to act as powerful transactivators (Evans, 1988, supra). In order to test the hypothesis that Rip-1 is either a member, or part of a complex containing a member of the glucocorticosteroid receptor superfamily, we tested the effects of different steroid hormones on Rip-1 translocation. Both Dexamethasone (at $10^{-6}$M) and Hydrocortisone ($10^{-6}$M) (activators of GR II pathway), but neither 9-cis-retinoic acid nor all-trans-retinoic acid (activators of RAR and related pathways) induced the nuclear translocation of Rip-1. Furthermore, cholesterol (cyclodextrin conjugated), and cyclodextrin, also failed to induce the nuclear translocation of Rip-1.

Vpr and Rip-1 co-immunoprecipitated with hGR

The possibility that Rip-1 is a novel member of the GR type II receptor family does not exclude the alternative in which Vpr and/or Rip-1 form a part of the GR transcription complex. Resting cells have most of their GR in their cytoplasmic portion, associated with a heat shock protein 90 dimer, and hsp56. Upon activation, the receptor is transformed and the complex changes in its molecular composition. It is conceivable that vpr alters Rip-1 such that it binds GR, and/or some other member of the complex in order to promote receptor transformation and the subsequent nuclear translocation. Accordingly, we stimulated resting U937 cells, or supplemented resting cells' lysates with Vpr. The cells, or lysates, respectively, were then exposed to a reversible (DTSSP), or a nonreversible crosslinking agent (DSS) followed by immunoprecipitation of GR using mouse anti-hGR (Affinity bioreagents) coupled protein D beads. These samples were subsequently analyzed by SDS-PAGE, western blot. In addition, the fractions which were crosslinked with DSS show that GR as well as Vpr and Rip-1 are involved in a high molecular weight complex.

Vpr mutant viruses are complemented in trans by Vpr protein and GR II stimulating steroids The effect of glucocorticosteroids on the nonproductively infected U937 cells described earlier was examined. HIV-1 NL43 Δvpr viruses were complemented in trans by addition of either Vpr protein, Dexamethasone, or Hydrocortisone to the tissue culture medium. This mutant virus however was not affected by the addition of either type of retinoic acid used, nor by cholesterol or cyclodextrin. The two glucocorticosteroids studied were also able to increase virus production in U937 cells infected with the wild type molecular clone, HIV-1 NL43. This is an effect very similar to that which has been observed for exogenous Vpr protein. GR type II activators in an analogous manner to Vpr, whether virion borne or added exogenously mediated Rip-1 cytoplasmic to nuclear translocation. The kinetics of this translocation process are consistent with the observed GR type II activation of viral protein production.

GR II inhibitors affect the Vpr mediated effects on Rip-1 and virus production

Specific inhibitors of GR II translocation and cellular activation have been previously described (reviewed in Agarwal, et al., 1987, Glucocorticoid Antagonists. FEBS letters. 217, 221–226; Baulieu, 1991, The Steroid Hormone Antagonist RU486. Endocrinology and Metabolism. 20, 873; Gronemeyer, et al., 1992, Mechanisms of Antihormone Action. J. Steroid Biochem. 41, 217–221). Mifepristone has been reported to reverse the catabolic effect of glucocorticoids in thymocytes in vitro (Lazar and Agarwal, 1986, Evidence for an antagonist specific receptor that does not bid mineralocorticoid agonists. Biochem Biophys Res Commun. 134, 261–265), by inhibiting the formation and translocation of the dexamethasone-receptor complexes as well as nuclear translocation (Lazar and Agarwal, 1986, supra; Lindenmeyer, et al., 1990, Glucocorticoid Receptor Monoclonal Antibodies Define the Biological Action of RU38486 in Intact 1316 Melanoma Cells. Cancer yes. 50, 7985–7991). Mifepristone can also inhibit the induction of Epstein-Barr virus in Daudi cells (Dietrich, et al., 1986, Antagonism of glucocorticoid induction of Epstein-Barr virus early antigens by different steroids in Daudi lymphoma cells. J. Steroid Biochem. 24, 417–421), as well as reverse the Dexamethasone-induced inhibition of growth in a human cervical-carcinoma cell line (Bakke, 1986, Antagonistic effect of glucocorticoids on retinoic acid induced growth inhibition and morphological alterations of a human cell line. Cancer Res. 46, 1275–1279). The biology of Rip-1 in the presence of a specific inhibitor of the GR II pathway (mifepristone) was analyzed. The nuclear translocation of Rip-1 induced by Dexamethasone and Hydrocortisone was blocked through the addition of mifepristone to the culture medium. Similarly, Vpr induced translocation of Rip-1 was also inhibited by the exposure of these cells to mifepristone.

The effects of these compounds and those of Vpr on virus production were also curtailed by this glucocorticosteroid receptor inhibitor. The levels of virus produced by HIV-1 infected cells exposed to mifepristone was about 70% lower than the untreated cultures. Mifepristone was also able to inhibit the enhancement in virus production observed by the addition of Vpr protein to infected cells (ca. −80–90% inhibition). Furthermore, the transcomplementation observed for the HIV-1 NL43 Δvpr infected U937 cells by Vpr protein was also abolished by mifepristone treatment, yielding virus levels similar to those observed in the nonproductively infected cultures. The mifepristone inhibitory effects were observed to be dose responsive. The concentration selected for most of the inhibition studies described was $10^{-6}$M.

Vpr and GR II stimulating steroids induce LTR mediated gene expression, which is inhibitable by mifepristone Though glucocorticoid receptors have been defined to function as powerful transcription factors, and Vpr has been shown to weakly transactivate the HIV LTR and several heterologous viral promoters, there is however no evidence for a direct interaction between the vpr gene product and the HIV LTR (Cohen, et al., 1990b, supra). The possibility that activation of the GR pathway could play a central role in the viral transcription process was considered. To test this, RD cells were transfected with an LTR-CAT encoding plasmid (pBennCAT) (Gendelman, 1986, supra), without selection. 12 hours later, the cell monolayers were washed and fresh medium containing the test reagents was added to the cultures, and 48 hours later the cells were harvested. In these studies, the co-transfection of a Vpr encoding plasmid with the LTR-CAT encoding plasmid produced an increase in CAT activity of 5–10 fold over the controls, as has been previously reported. In contrast, the increase in CAT activity observed with the addition of exogenous Vpr protein to the LTR-CAT transfected cells was 60–85 fold. When a set of cells were transfected with the LTR-CAT encoding plasmid, and a second set of cells were transfected with the vpr-encoding plasmid, were brought into proximity by the presence of a 0.22 μm diameter pore membrane, an increase of 25–40 fold in CAT activity over the controls was observed. Vpr protein was detected in the tissue culture media of these cells, as assessed by capture ELISA. These data support that exogenous Vpr protein can enhance HIV replication in vitro through its transactivating activity.

It is likely that Vpr manifests its activity through the GRE binding element of the HIV-1 LTR thus affecting viral transcription. This was examined directly using HIV-1 LTR-CAT constructs. The site on the HIV-LTR to which the Vpr mediated transactivation was mapped. Using a panel of deletion mutant LTR-CAT constructs, both Vpr and Dexamethasone, were able to induce CAT activity as long as the region between −250 to −264 were present. This is the region which has been defined to contain a possible GRE sequence. In addition, Vpr protein was able to stimulate CAT expression from cells transfected with pGRE5/CAT (USB), a plasmid in which the CAT gene is preceded by five consecutive GRE sequences, upstream from the transcriptional start sequence.

Dexamethasone and Hydrocortisone were observed to stimulate levels of CAT activity similar to those attained by Vpr protein treatment (ca. 50 fold over the controls). These levels of CAT activity were approximately ten times higher than the levels of CAT activity stimulated by cotransfection of pBennCat with Vpr-pBabePuro. In addition, the increase in CAT activity stimulated by either Vpr protein, or steroids, was inhibited by supplementing these cultures with mifepristone. Furthermore, mifepristone blocked the more modest increase in CAT activity which was observed in cells cotransfected with a Vpr encoding plasmid and the LTR-CAT plasmid. In addition, neither 9-cis-retinoic acid, nor all-trans retinoic acid induced any increases in CAT activity above basal levels.

Induction of the GRE-DNA binding complex by Vpr

In order to probe the observation that the Vpr mediated transactivating activity maps to the region of the HIV-LTR where the GRE sequences were shown to be encoded, the possibility that Vpr was inducing the binding of the GR transcriptional complex to the precise GRE sequence derived from the LTR was tested. Oligodeoxynucleotide probes were synthesized whose sequences were derived from LTR's of HIV-1, HIV-2, MMTV viruses, or an irrelevant viral promoter source. Vpr protein added to cell lysates was observed to induce the binding of a protein complex to the specific GRE sequences of HIV-1/2. This DNA-binding complex induced by Vpr stimulation was identical in its migration characteristics to the complex induced by Dexamethasone stimulation. This binding could be completely competed by a 100 molar excess of unlabelled MMTV GRE oligodeoxynucleotide, but was not diminished at all by the irrelevant oligodeoxynucleotide.

Example 2

The amino acid sequence of Vpr is disclosed in U.S. Ser. No. 08/167,608 filed Dec. 15, 1993, which is incorporated herein by reference. Fragments of Vpr which bind to Rip-1 comprise Vpr residues 27–39, 35–48, 41–55, 49–60 and/or 66–68.

Some embodiments of the invention are fragments of Vpr which comprise at least three amino acids and which bind to Rip-1. In some embodiments, fragments of Vpr are less than 50 amino acids. In some embodiments, fragments of Vpr are less than 25 amino acids. In some embodiments, fragments of Vpr are less than 20 amino acids. In some embodiments, fragments of Vpr are less than 15 amino acids. In some embodiments, fragments of Vpr are less than 13 amino acids. In some embodiments, fragments of Vpr are less than 10 amino acids. In some embodiments, fragments of Vpr are less than 8 amino acids. In some embodiments, fragments of Vpr are less than 5 amino acids. In some embodiments, fragments of Vpr are less than 4 amino acids.

Some embodiments of the invention are peptides which comprise fragments of Vpr which comprise at least three amino acids and which bind to Rip-1. In some embodiments, the peptides are less then 25 amino acids. In some embodiments, the peptides are less then 2 amino acids. In some embodiments, the peptides comprise fragments of Vpr that are less than 25 amino acids. In some embodiments, the peptides comprise fragments of Vpr that are less than 20 amino acids. In some embodiments, the peptides comprise fragments of Vpr that are less than 15 amino acids. In some embodiments, the peptides comprise fragments of Vpr that are less than 10 amino acids. In some embodiments, the peptides comprise fragments of Vpr that are less than 8 amino acids. In some embodiments, the peptides comprise fragments of Vpr that are less than 5 amino acids. In some embodiments, the peptides comprise fragments of Vpr that are less than 4 amino acids.

In some embodiments, the compounds of the present invention are: 20 amino acids or less; consist of or comprise a fragment of Vpr that is at least 3 amino acids and that binds to Rip-1; and are useful as activators or inhibitors of GR type II translocation. The peptides of the invention comprise amino acid sequences that consist of 20 amino acids or less, preferably 10–15 amino acids or less. As used herein, the term "compound" refers to molecules which include peptides and non-peptides including, but not limited to molecules which comprise amino acid residues joined by at least some non-peptidyl bonds. As used herein, the term "peptide" refers to polypeptides formed from amino acid subunits joined by native peptide bonds. The term "amino acid" is meant to refer to naturally occurring amino acid moieties and to moieties which have portions similar to naturally occurring peptides but which have non-naturally occurring portions. Thus, peptides may have altered amino acids or linkages. Peptides may also comprise other modifications consistent with the spirit of this invention. Such peptides are best described as being functionally interchangeable yet structurally distinct from natural peptides. As used herein, the terms "compounds" and "peptides" are used interchangeably.

Conservative substitutions of amino acid sequences of Vpr fragments are contemplated. As used herein, the term "conservative substitutions" is meant to refer to amino acid substitutions of Vpr residues with other residues which share similar structural and/or charge features. Those having ordinary skill in the art can readily design Vpr fragments with conservative substitutions for amino acids based upon well known conservative groups.

Because most enzymes involved in degradation recognize a tetrahedral alpha-carbon, the D-amino acids may be utilized in order to avoid enzyme recognition and subsequent cleavage. Peptides comprised of D amino acids are less susceptible to degradation. In some embodiments of the present invention, compounds comprising D amino acids are provided which comprise the same amino acid sequences as those presented throughout this disclosure but in reverse order, i.e. from the carboxy terminus to the amino terminus. Thus, the present disclosure is meant to specifically encompass each of the sequences set out herein as additionally describing peptides from the carboxy terminus to the amino terminus which comprising D amino acids.

In some embodiments, D amino acid residues are provided to facilitate the proper folding and circularization. In such cases, one or more D amino acid residues are provided with the remainder being L amino acids. Likewise, in some embodiments, L amino acid residues are provided to facilitate the proper folding and circularization of peptides composed mostly of D amino acids. In such cases, one or more L amino acid residues are provided with the remainder being D amino acids.

Peptides of some embodiments of the present invention may be from at least about 3 to up to about 20 amino acids in length. In some embodiments of the present invention, peptides of the present invention are from about 5 to about 15 amino acids in length. In preferred embodiments of the present invention peptides of the present invention are 4, 5, 6, 7, 8, 9, 10, 11, 12, 13, 14 15, 16, 17, 18 or 19 amino acids in length. It is preferred that peptides are as small as possible.

In peptides of the invention, at least 3 amino acids of the peptide is a Vpr fragment. It is preferred that the Vpr derived portion makes up at least 10% of the amino acid sequence of the peptide. In some embodiments, it is preferred that greater than about 20–25% of the amino acid sequence of the peptides of the present invention are Vpr derived, more preferably 30–40% and more preferably greater than 50%. In some embodiments, the proportion of amino acid sequence of the peptides of the present invention that are Vpr derived approaches about 60% or about 75% or more.

Synthesized peptides of the invention may be circularized in order to mimic the geometry of those portions as they occur in Vpr. Circularization may be facilitated by disulfide bridges between cysteine residues. Cysteine residues may be included in positions on the peptide which flank the portions of the peptide which are derived from Vpr. Cysteine residues within the portion of a peptide derived from Vpr may be deleted and/or conservatively substituted to eliminate the formation of disulfide bridges involving such residues. Alternatively, other means of circularizing peptides are also well known. The peptides may be circularized by means of covalent bonds, such as amide bonds, between amino acid residues of the peptide such as those at or near the amino and carboxy termini.

In some embodiments of the invention, peptides consist of 15 amino acid residues or less and are circularized or otherwise conformationally restricted by disulfide bonds arising from N- and C-terminal cysteines.

The peptides of the present invention may be prepared by any of the following known techniques. Conveniently, the peptides may be prepared using the solid-phase synthetic technique initially described by Merrifield, in *J. Am. Chem. Soc.*, 15:2149–2154 (1963) which is incorporated herein by reference. Other peptide synthesis techniques may be found, for example, in M. Bodanszky et al., (1976) *Peptide Synthesis*, John Wiley & Sons, 2d Ed. which is incorporated herein by reference; Kent and Clark-Lewis in *Synthetic Peptides in Biology and Medicine*, p. 295–358, eds. Alitalo, K., et al. Science Publishers, (Amsterdam, 1985) which is incorporated herein by reference; as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984) which is incorporated herein by reference. The synthesis of peptides by solution methods may also be used, as described in *The Proteins, Vol. II*, 3d Ed., p. 105–237, Neurath, H. et al., Eds., Academic Press, New York, N.Y. (1976) which is incorporated herein by reference. Appropriate protective groups for use in such syntheses will be found in the above texts, as well as in J. F. W. McOmie, *Protective Groups in Organic Chemistry*, Plenum Press, New York, N.Y. (1973) which is incorporated herein by reference.

In general, these synthetic methods involve the sequential addition of one or more amino acid residues or suitable protected amino acid residues to a growing peptide chain. Normally, either the amino or carboxyl group of the first amino acid residue is protected by a suitable, selectively-removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

The peptides can be tested following the methods herein to determine whether they bind to Rip-1 and induce GR type II complex translocation or whether they bind to Rip-1 and inhibit GR type II complex translocation. Those peptides which bind to Rip-1 and induce GR type II complex translocation are useful as non-steroidal alternatives in the treatment of conditions, diseases and disorders in which steroid administration is typically indicated. Those peptides which bind to Rip-1 and induce GR type II complex translocation are useful in the treatment of conditions, diseases and disorders in which glucocorticoid antagonist administration is typically indicated. Inhibitors are particularly useful as anti-HIV compounds if they compete with Vpr to bind to Rip-1 but do not induce GR type II complex translocation.

The present invention provides pharmaceutical compositions that comprise the compounds of the invention and pharmaceutically acceptable carriers or diluents. The pharmaceutical composition of the present invention may be formulated by one having ordinary skill in the art with compositions selected depending upon the chosen mode of administration. Suitable pharmaceutical carriers are described in *Remington's Pharmaceutical Sciences*, A. Osol, a standard reference text in this field. In carrying out methods of the present invention, peptides of the present invention can be used alone or in combination with other diagnostic, therapeutic or additional agents. Such additional agents include excipients such as flavoring, coloring, stabilizing agents, thickening materials, osmotic agents and anti-bacterial agents. Such agents may enhance the peptide's use in vitro, the stability of the composition during storage, or other properties important to achieving optimal effectiveness.

For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions of the present invention may be administered by any means that enables the active agent to reach the targeted cells. Because peptides are subject to being digested when administered orally, parenteral administration, i.e., intravenous, subcutaneous, transdermal, intramuscular, would ordinarily be used to optimize absorption. Intravenous administration may be accomplished with the aid of an infusion pump. The pharmaceutical compositions of the present invention may be formulated as an emulsion. Alternatively, they may be formulated as aerosol medicaments for intranasal or inhalation administration. In some cases, topical administration may be desirable.

The dosage administered varies depending upon factors such as: pharmacodynamic characteristics; its mode and route of administration; age, health, and weight of the recipient; nature and extent of symptoms; kind of concurrent treatment; and frequency of treatment. Usually, the dosage of peptide can be about 1 to 3000 milligrams per 50 kilograms of body weight; preferably 10 to 1000 milligrams per 50 kilograms of body weight; more preferably 25 to 800 milligrams per 50 kilograms of body weight. Ordinarily 8 to 800 milligrams are administered to an individual per day in divided doses 1 to 6 times a day or in sustained release form is effective to obtain desired results.

Depending upon the disease or disorder to be treated, the pharmaceutical compositions of the present invention may be formulated and administered to most effectively. Modes of administration will be apparent to one skilled in the art in view of the present disclosure.

Example 3

Other fragments of Vpr which bind to Rip-1 and are useful as either inducers of GR type II complex translocation or inhibitors of GR type II complex translocation can be identified by synthesizing nested peptide fragments of Vpr and testing them for transactivating or inhibitory activity.

Nested peptides fragments of Vpr protein may be produced and tested for translocation inducing or inhibitory activity. Nested peptides may be 3–30 amino acids in length and preferably 4, 5, 6, 7, 8, 9, 10, 11, 12, 13, 14, 15, 16, 17, 18, 19 or 20 amino acids in length. Peptides may be tested for translocation inducing or inhibitory activity as described above. Peptides may be prepared which comprise Vpr fragments identified as inducers or inhibits of translocation activity as described above.

---

We claim:

1. An in vitro method of identifying compounds that induce glucocorticoid receptor type II (GR-II) and viral protein R interacting protein (Rip-1) complex translocation comprising the following steps:

a) preparing cells expressing Rip-1 and the GR-II wherein Rip-1 and GR-II are capable of forming a cytosolic Rip-1/GR-II receptor complex;

b) contacting said cells with a test compound capable of inducing Rip-1/GR-II receptor complex cytoplasmic to nuclear translocation;

c) detecting the level of Rip-1/GR-II receptor cytoplasmic to nuclear translocation in said cells in the presence of the test compound; and, d) performing a control assay that detects the level of Rip-I/GR-II receptor complex nuclear translocation in the absence of said test compound;

wherein detection of a higher level of cytoplasmic to nuclear translocation of the Rip-1/GR-II receptor complex is indicative of said compound being capable of inducing Rip-1/GR-II receptor complex translocation.

2. The method of claim 1 wherein Rip-1/GR-II receptor complex nuclear translocation is detected through the subcellular fractionation of said cells into soluble and insoluble antigen-containing fractions, followed by the addition of Rip-1-specific antibodies to each fraction.

3. The method of claim 2 wherein said antibodies contain a radioactive label, fluorescent label, or enzymatic label.

4. The method of claim 2 wherein the soluble and insoluble antigen-containing fractions are attached to a solid support.

5. An in vitro method of inducing glucocorticoid receptor type II (GR-II) and viral protein R interacting protein (Rip-1) complex nuclear translocation in cells comprising the following steps:

a) preparing cells expressing Rip-1 and GR-II wherein said proteins are capable of forming a cytosolic Rip-1/GR-II receptor complex; and, b) contacting said cells with the human immunodeficiency virus type 1 (HIV-1) Vpr protein under conditions wherein said Vpr protein binds to the cytosolic Rip-1/GR-II receptor complex thereby generating a Vpr/Rip-1/GR-II complex that subsequently undergoes cytoplasmic to nuclear translocation.

* * * * *